United States Patent
Jaffray et al.

(10) Patent No.: US 9,087,224 B2
(45) Date of Patent: Jul. 21, 2015

(54) SYSTEM AND METHOD FOR COMMISSIONING OF A BEAM MODEL FOR A THREE DIMENSIONAL RADIATION THERAPY TREATMENT PLANNING SYSTEM

(75) Inventors: David Anthony Jaffray, Etobicoke (CA); Daniel Letourneau, Toronto (CA); Michael Bryan Sharpe, Mississauga (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 382 days.

(21) Appl. No.: 13/018,688

(22) Filed: Feb. 1, 2011

(65) Prior Publication Data
US 2011/0191085 A1    Aug. 4, 2011

Related U.S. Application Data
(60) Provisional application No. 61/300,606, filed on Feb. 2, 2010.

(51) Int. Cl.
*A61N 5/10* (2006.01)
*G06G 7/60* (2006.01)
*G01T 1/29* (2006.01)

(52) U.S. Cl.
CPC .............. *G06G 7/60* (2013.01); *A61N 5/1075* (2013.01); *G01T 1/2914* (2013.01)

(58) Field of Classification Search
CPC ...... A61N 5/1048; A61N 5/1075; G01T 1/29; G01T 1/2914; G01T 7/005
USPC .......................................................... 378/65
See application file for complete search history.

(56) References Cited

U.S. PATENT DOCUMENTS

| | | | | |
|---|---|---|---|---|
| 5,027,818 A * | 7/1991 | Bova et al. | ..... | 600/427 |
| 6,393,096 B1 * | 5/2002 | Carol et al. | ..... | 378/65 |
| 6,661,871 B2 * | 12/2003 | Siochi | ..... | 378/65 |
| 6,714,620 B2 * | 3/2004 | Caflisch et al. | ..... | 378/65 |
| 6,853,705 B2 * | 2/2005 | Chang | ..... | 378/65 |
| 6,993,112 B2 * | 1/2006 | Hesse | ..... | 378/65 |
| 7,085,348 B2 * | 8/2006 | Kamath et al. | ..... | 378/65 |
| 7,142,635 B2 * | 11/2006 | Kamath et al. | ..... | 378/65 |
| 7,283,611 B1 * | 10/2007 | Luan et al. | ..... | 378/65 |
| 7,289,599 B2 * | 10/2007 | Seppi et al. | ..... | 378/65 |
| 8,130,905 B1 * | 3/2012 | Nelms | ..... | 378/65 |
| 2002/0106054 A1 * | 8/2002 | Caflisch et al. | ..... | 378/65 |

(Continued)

OTHER PUBLICATIONS

MapCHECK User's Guide. Melbourne, Florida, USA: Sun Nuclear Corporation; 2004.

(Continued)

*Primary Examiner* — Thomas R Artman
(74) *Attorney, Agent, or Firm* — Norton Rose Fulbright Canada LLP

(57) ABSTRACT

A system and method for commissioning of a beam model for a three dimensional radiation therapy treatment planning system is described. The system includes an intensity modulated radiotherapy (IMRT) unit for generating a two dimensional intensity modulated beam pattern, a two dimensional diode array for detecting a two dimensional dose map for the beam pattern, and a processor configured to execute instructions for iteratively adjusting one or more parameters for the beam model, in order to increase agreement between the detected dose map and a calculated dose map calculated using the beam model.

14 Claims, 10 Drawing Sheets

(56) References Cited

U.S. PATENT DOCUMENTS

| | | | |
|---|---|---|---|
| 2009/0252292 A1* | 10/2009 | Simon et al. | 378/65 |
| 2010/0054413 A1* | 3/2010 | Sobering et al. | 378/65 |
| 2010/0082294 A1* | 4/2010 | Adnani | 702/182 |
| 2011/0191085 A1* | 8/2011 | Jaffray et al. | 703/11 |

OTHER PUBLICATIONS

D. Letourneau, J. Publicover, J. Kozelka, D. J. Moseley, D. A. Jaffray, "Novel dosimetric phantom for quality assurance of volumetric modulated arc therapy," Med Phys. 36, 1813-1821 (2009).

C. G. Rowbottom, D. A. Jaffray, "Development of an integral system test for image-guided radiotherapy," Med Phys. 31, 3500-3505 (2004).

T. Bortfeld, W. Schlegel, B. Rhein, "Decomposition of pencil beam kernels for fast dose calculations in three-dimensional treatment planning," Med Phys. 20, 311-318 (1993).

J. D. Bourland, E. L. Chaney, "A finite-size pencil beam model for photon dose calculations in three dimensions," Med Phys. 19, 1401-1412 (1992).

A. Gustafsson, B. K. Lind, A. Brahme, "A generalized pencil beam algorithm for optimization of radiation therapy," Med Phys. 21, 343-356 (1994).

O. Z. Ostapiak, Y. Zhu, J. Van Dyk, "Refinements of the finite-size pencil beam model of three-dimensional photon dose calculation," Med Phys. 24, 743-750 (1997).

A. Ahnesjo, "Collapsed cone convolution of radiant energy for photon dose calculation in heterogeneous media," Med Phys. 16, 577-592 (1989).

T. R. Mackie, J. W. Scrimger, J. J. Battista, "A convolution method of calculating dose for 15-MV x rays," Med Phys. 12, 188-196 (1985).

N. Papanikolaou, T. R. Mackie, C. Meger-Wells, M. Gehring, P. Reckwerdt, "Investigation of the convolution method for polyenergetic spectra," Med Phys. 20, 1327-1336 (1993).

J. J. Battista, M. B. Sharpe, "True three-dimensional dose computations for megavoltage x-ray therapy: a role for the superposition principle," Australas Phys Eng Sci Med. 15, 159-178 (1992).

M. B. Sharpe, D. A. Jaffray, J. J. Battista, P. Munro, "Extrafocal radiation: a unified approach to the prediction of beam penumbra and output factors for megavoltage x-ray beams," Med Phys. 22, 2065-2074 (1995).

J. J. Demarco, T. D. Solberg, J. B. Smathers, "A CT-based Monte Carlo simulation tool for dosimetry planning and analysis," Med Phys. 25, 1-11 (1998).

D. M. Lovelock, C. S. Chui, R. Mohan, "A Monte Carlo model of photon beams used in radiation therapy," Med Phys. 22, 1387-1394 (1995).

C. M. Ma, E. Mok, A Kapur, T. Pawlicki, D. Findley, S. Brain, K. Forster, A. L. Boyer, "Clinical implementation of a Monte Carlo treatment planning system," Med Phys. 26, 2133-2143 (1999).

D. W. Rogers, B. A. Faddegon, G. X. Ding, C. M. Ma, J. We, T. R. Mackie, "BEAM: a Monte Carlo code to simulate radiotherapy treatment units," Med Phys. 22, 503-524 (1995).

L. Wang, C. S. Chui, M. Lovelock, "A patient-specific Monte Carlo dose-calculation method for photon beams," Med Phys. 25, 867-878 (1998).

A. Ahnesjo, L. Weber, A. Murman, M. Saxner, I. Thorslund, E. Traneus, "Beam modeling and verification of a photon beam multisource model," Med Phys. 32, 1722-1737 (2005).

F. M. Khan. The Physics of Radiation Therapy. Second ed. Baltimore, Maryland, USA: Williams and Wilkins; 176-225 (1994).

B. Fraass, K. Doppke, M. Hunt, G. Kutcher, G. Starkschall, R. Stern, J. Van Dyke, "American Association of Physicists in Medicine Radiation Therapy Committee Task Group 53: quality assurance for clinical radiotherapy treatment planning," Med Phys. 25, 1773-1829 (1998).

G. Starkschall, R. E. Steadham, Jr., R. A. Popple, S. Ahmad, Rosen, II, "Beam-commissioning methodology for a three-dimensional convolution/superposition photon dose algorithm," J Appl Clin Med Phys. 1, 8-27 (2000).

J. Van Dyk, R. B. Barnett, J. E. Cygler, P. C. Shragge, "Commissioning and quality assurance of treatment planning computers," Int J Radiat Oncol Biol Phys. 26, 261-273 (1993).

J. Venselaar, H. Welleweerd, B. Mijnheer, "Tolerances for the accuracy of photon beam dose calculations of treatment planning systems," Radiother Oncol. 60, 191-201 (2001).

J. L. Bedford, P. J. Childs, V. Nordmark Hansen, M. A. Mosleh-Shirazi, F. Verhaegen, A. P. Warrington, "Commissioning and quality assurance of the Pinnacle(3) radiotherapy treatment planning system for external beam photons," Br J Radiol. 76, 163-176 (2003).

A. Rangel, N. Ploquin, I. Kay, P. Dunscombe, "Towards an objective evaluation of tolerances for beam modeling in a treatment planning system," Phys Med Biol. 52, 6011-6025 (2007).

W. A. Tome, "Beam modeling for a convolution/superposition-based treatment planning system," Med Dosim. 27, 11-19 (2002).

W. U. Laub, T. Wong, "The volume effect of detectors in the dosimetry of small fields used in IMRT," Med Phys. 30, 341-347 (2003).

G. Yan, C. Fox, C. Liu, J. G. Li, "The extraction of true profiles for TPS commissioning and its impact on IMRT patient-specific QA," Med Phys. 35, 3661-3670 (2008).

E. L. Chang, A. S. Shiu, E. Mendel, L. A. Mathews, A. Mahajan, P. K. Allen, J. S. Weinberg, B. W. Brown, X. S. Wang, S. Y. Woo, C. Cleeland, M. H. Maor, L. D. Rhines, "Phase I/II study of stereotactic body radiotherapy for spinal metastasis and its pattern of failure," J Neurosurg Spine. 7, 151-160 (2007).

P. C. Gerszten, S. A. Burton, C. Ozhasoglu, W. C. Welch, "Radiosurgery for spinal metastases: clinical experience in 500 cases from a single institution," Spine (Phila Pa 1976). 32, 193-199 (2007).

A. Sahgal, C. Ames, D. Chou, L. Ma, K. Huang, W. Xu, C. Chin, V. Weinberg, C. Chuang, P. Weinstein,. D. A. Larson, "Stereotactic body radiotherapy is effective salvage therapy for patients with prior radiation of spinal metastases," Int J Radiat Oncol Biol Phys. 74, 723-731 (2009).

Y. Yamada, M. H. Bilsky, D. M. Lovelock, E. S. Venkatraman, S. Toner, J. Johnson, J. Zatcky, M. J. Zelefsky, Z. Fuks, "High-dose, single-fraction image-guided intensity-modulated radiotherapy for metastatic spinal lesions," Int J Radiat Oncol Biol Phys. 71, 484-490 (2008).

J. A. Nelder, R. Mead, "A simplex method for function minimization," Computer Journal. 7, 308-313 (1965).

A. Antoniou, W. S. Lu. Practical Optimization. Algorithms and Engineering Applications. New York: Springer; 281-284 (2007).

ICRU. Use of computers in external beam radiotherapy procedures with high-energy photons and electrons. Report No. 42. Washington, DC: International Commission on Radiation Units and Measurements; 49-51 (1987).

A. S. Shiu, S. Tung, K. R. Hogstrom, J. W. Wong, R. L. Gerber, W. B. Harms, J. A. Purdy, R. K. Ten Haken, D. L. McShan, B. A. Fraass, "Verification data for electron beam dose algorithms," Med Phys. 19, 623-636 (1992).

D. Letourneau, H. Keller, M. B. Sharpe, D. A. Jaffray, "Integral test phantom for dosimetric quality assurance of image guided and intensity modulated stereotactic radiotherapy," Med Phys. 34, 1842-1849 (2007).

D. A. Jaffray, J. J. Battista, A. Fenster, P. Munro, "X-ray sources of medical linear accelerators: focal and extra-focal radiation," Med Phys. 20, 1417-1427 (1993).

S. L. Breen, D. J. Moseley, B. Zhang, M. B. Sharpe, "Statistical process control for IMRT dosimetric verification," Med Phys. 35, 4417-4425 (2008).

D. E. Lighter, D. C. Fair. Principles and Methods of Quality Management in Health Care. Gaithersburg, MD: Aspen;109-114 (2000).

D. Letourneau, M. Gulam, D. Yan, M. Oldham, J. W. Wong, "Evaluation of a 2D diode array for IMRT quality assurance," Radiother Oncol. 70, 199-206 (2004).

* cited by examiner

| Available for optimization | | Not available for optimization |
|---|---|---|
| Description | Abbreviation (units) | Description |
| - MLC transmission | $\%T_{MLC}$ (%) | - Energy spectrum |
| - Jaw transmission | $\%T_{X\text{-jaws}}$ and $\%T_{Y\text{-jaws}}$ (%) | - Electron contamination |
| - MLC interleaf leakage | $L_{height}$ and $L_{width}$ (% and cm) | - Horn's shape |
| - Orthogonal source size | $S_X$ and $S_Y$ (cm) | |
| - Extra-focal scatter source | $G_{height}$ and $G_{width}$ (% and cm) | |
| - Geometric correction for rounded leaf MLC leaf end | Pos(x) (cm) | |

FIG. 2

| Beam Model Parameters | | Initial Beam Model | Optimized Beam Model |
|---|---|---|---|
| MLC transmission: | $\%T_{MLC}$ (%) | 0.400 | 0.175 |
| Jaw transmission: | $\%T_{X\text{-jaws}}$ (%) | 0.400 | 1.590 |
| | $\%T_{Y\text{-jaws}}$ (%) | 0.400 | 1.590 |
| MLC interleaf leakage: | $L_{height}$ (%) | 2.000 | 2.208 |
| | $L_{width}$ (cm) | 0.150 | 0.071 |
| Orthogonal source size: | $S_X$ (cm) | 0.035 | 0.066 |
| | $S_Y$ (cm) | 0.035 | 0.042 |
| Extra-focal scatter source: | $G_{height}$ (%) | 8.500 | 8.500 |
| | $G_{width}$ (cm) | 1.850 | 1.850 |
| Second degree polynomial: | a | $-1.140 \times 10^{-3}$ | $-1.630 \times 10^{-3}$ |
| (Rounded leaf-end correction) | b | $-1.530 \times 10^{-5}$ | $-1.530 \times 10^{-5}$ |
| | c | $6.996 \times 10^{-2}$ | $6.235 \times 10^{-2}$ |

FIG. 5

| Mean difference (± SD) | Target | | | Organ at risk | | |
|---|---|---|---|---|---|---|
| | Initial Model | Optimized Model | Test for statistical difference | Initial Model | Optimized Model | Test for statistical difference |
| Prostate cases (n = 25 patients) | 0.3% ± 1.2% | 0.8% ± 1.1% | p < 0.001 (Wilcoxon) | -3.5% ± 2.3% | -0.6% ± 1.7% | p < 0.001 (t-test) |
| Paraspinal cases (n = 25 patients) | -4.2% ± 2.0 | -0.3% ± 2.3% | p < 0.001 (t-test) | -13.8% ± 6.9% | 2.0% ± 5.7% | p < 0.001 (t-test) |

FIG. 6

| Relative pass rate (± SD) | Initial Model | Optimized Model | Test for statistical difference |
|---|---|---|---|
| Prostate cases | | | p < 0.001 |
| (n = 175 beams) | 91.4% ± 4.1% | 98.2% ± 1.6% | (p < 0.001) |
| %DD/DTA: 3%/2mm | (73.1% ± 6.7%) | (89.4% ± 4.9%) | |
| (2%/1mm) | | | (Wilcoxon) |
| Paraspinal cases | | | p < 0.001 |
| (n = 214 beams) | 77.1% ± 9.7% | 96.4% ± 2.8% | (p < 0.001) |
| %DD/DTA: 3%/2mm | (48.8% ± 10.0%) | (77.8% ± 7.2%) | |
| (2%/1mm) | | | (Wilcoxon) |

FIG. 7

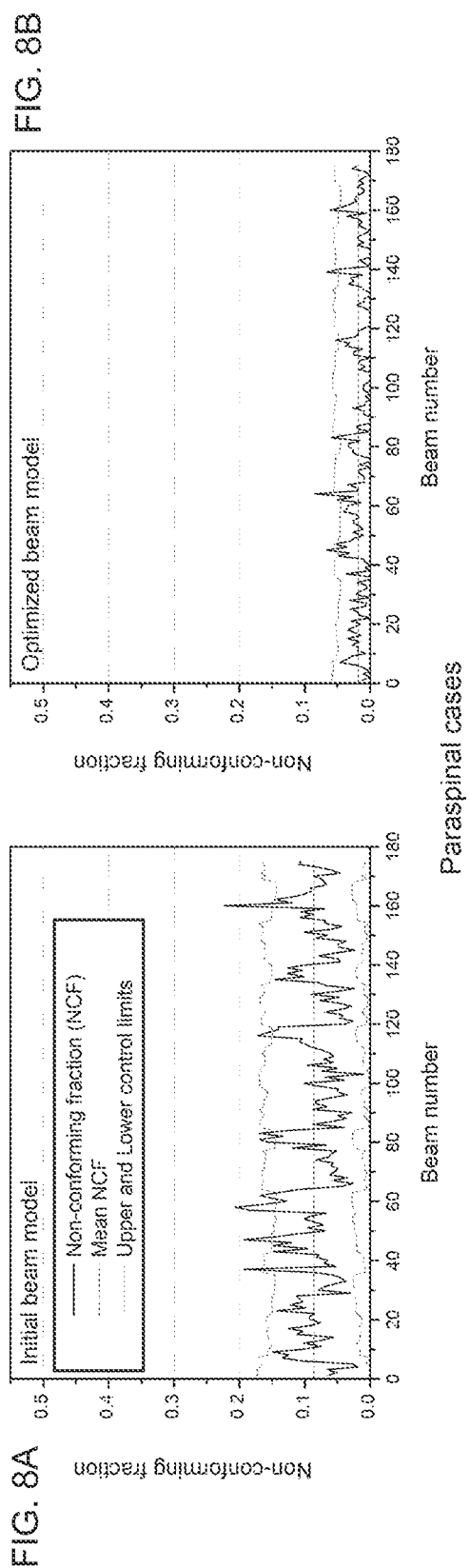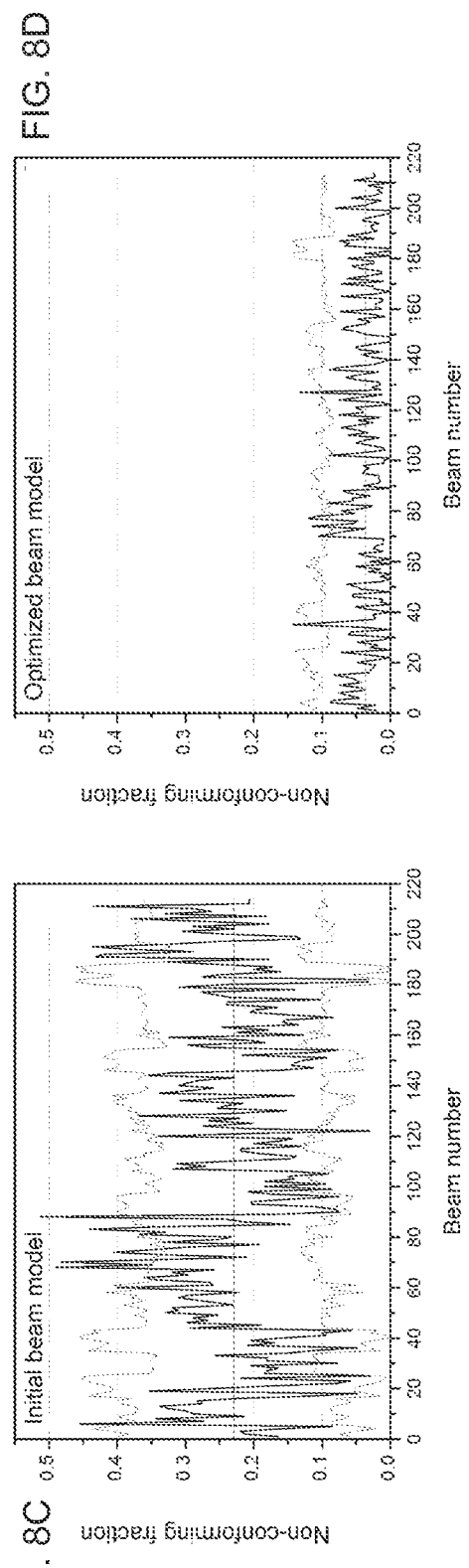
FIG. 8A / FIG. 8B — Prostate cases
FIG. 8C / FIG. 8D — Paraspinal cases

SYSTEM AND METHOD FOR COMMISSIONING OF A BEAM MODEL FOR A THREE DIMENSIONAL RADIATION THERAPY TREATMENT PLANNING SYSTEM

CROSS-REFERENCE TO RELATED APPLICATION

The present disclosure claims priority from U.S. provisional patent application No. 61/300,606, filed Feb. 2, 2010, the entirety of which is hereby incorporated by reference.

TECHNICAL FIELD

The present disclosure relates to radiation therapy treatment planning In particular, the present disclosure relates to commissioning of a beam model for a three dimensional radiation therapy treatment planning system.

BACKGROUND

In radiation therapy, a treatment planning system is often used to plan a treatment dosage for a patient. For high-energy photon radiotherapy, a three dimensional (3D) treatment planning system (TPS), for example using a pencil beam algorithm[1-4], a convolution/superposition algorithm[5-9] or a Monte Carlo algorithm[10-14], may rely on a virtual mechanical and dosimetric representation of a treatment unit called the beam model to calculate dose on a 3D representation of the patient. The commissioning of a beam model includes determining beam model parameters that generate a reasonable fit between delivered and planned dose in non-clinical irradiation conditions. The measurements used for commissioning include beam profiles and percent-depth dose (PDD) curves or tissue-phantom ratios[16] measured with an ion chamber and a scanning system in water. The evaluation of a beam model differs from dose calculation algorithm testing as it is performed in simple irradiation conditions (e.g., normal surface, rectangular fields and homogenous water phantom) and the observations can be fed back to the TPS to improve the agreement between planned and delivered dose. Published guidelines containing test procedures and acceptance criteria[17-20] are available to assist the clinical physicist in the commissioning of the beam model.

The accuracy of the dose calculation on a 3D representation of a patient depends in particular on the type of dose algorithm used in the TPS and the accuracy in beam model commissioning. In an example TPS, such as the Pinnacle³, version 8.0h, from Philips Medical Systems (Madison, Wis.), beam model commissioning includes the use of a series of TPS auto-model scripts for a first-order fit followed by manual adjustments of various beam model parameters in a trial and error process. The manual optimization of a beam model during commissioning can be a time consuming task due to its iterative and trial-and-error nature. Furthermore, the quality of the beam model commissioning depends on the user's ability to manage multiple parameters and assess their various impacts on the agreement between measured and calculated dose.

With the advent of intensity modulated radiotherapy (IMRT), the requirements on measured data for TPS commissioning and beam model accuracy have heightened. For example, the impact of accurate beam penumbra measurement on beam model and IMRT patient-specific quality control (QC) performance has been demonstrated[24, 25]. For high-dose and high-precision radiotherapy such as stereotactic body radiotherapy (SBRT) of paraspinal tumors[26-29], small geometric safety margins and high dose limits to critical organs at risk (OAR) stress the importance of beam model accuracy.

SUMMARY

In the context of high precision radiotherapy, it would be useful to provide a system and method for commissioning and/or optimization of the beam model. In the present disclosure, a system and method for commissioning a beam model for a three dimensional radiation therapy treatment planning system is described. The performance of an example system for commissioning of a beam model, in some examples based on IMRT beam measurements performed with an example two dimensional (2D) diode array, is also described.

In some aspects, there is provided a system for commissioning of a beam model for a three dimensional radiation therapy treatment planning system, the system comprising: an intensity modulated radiotherapy (IMRT) unit for generating a two dimensional intensity modulated beam pattern; a two dimensional diode array for detecting a two dimensional dose map for the beam pattern; and a processor configured to execute instructions for iteratively adjusting one or more parameters for the beam model, in order to increase agreement between the detected dose map and a calculated dose map calculated using the beam model.

In some aspects, there is provided a method for commissioning of a beam model for a three dimensional radiation therapy treatment planning system, the method comprising: obtaining a measured two dimensional dose map for a two dimensional intensity modulated beam pattern; iteratively adjusting one or more parameters for the beam model, in order to increase agreement between the measured dose map and a calculated dose map calculated using the beam model.

BRIEF DESCRIPTION OF THE DRAWINGS

Reference will now be made to the drawings, which show by way of example embodiments of the present disclosure, and in which:

FIG. 2 shows example beam model parameters for commissioning a beam model;

FIG. 5 shows a comparison of example beam model parameters between beam models commissioned using conventional methods and using an example of the disclosed method for commissioning a beam model for a 3D TPS;

FIG. 6 shows a comparison of the relative difference between Farmer chamber measurements and the planned dose between beam models commissioned using conventional methods and using an example of the disclosed method for commissioning a beam model for a 3D TPS;

FIG. 7 shows a comparison of measured and calculated dose maps between beam models commissioned using conventional methods and using an example of the disclosed method for commissioning a beam model for a 3D TPS;

FIGS. 8A-8D show charts comparing behavior of beam models commissioned using conventional methods and using an example of the disclosed method for commissioning a beam model for a 3D TPS;

DETAILED DESCRIPTION

Figure 1:
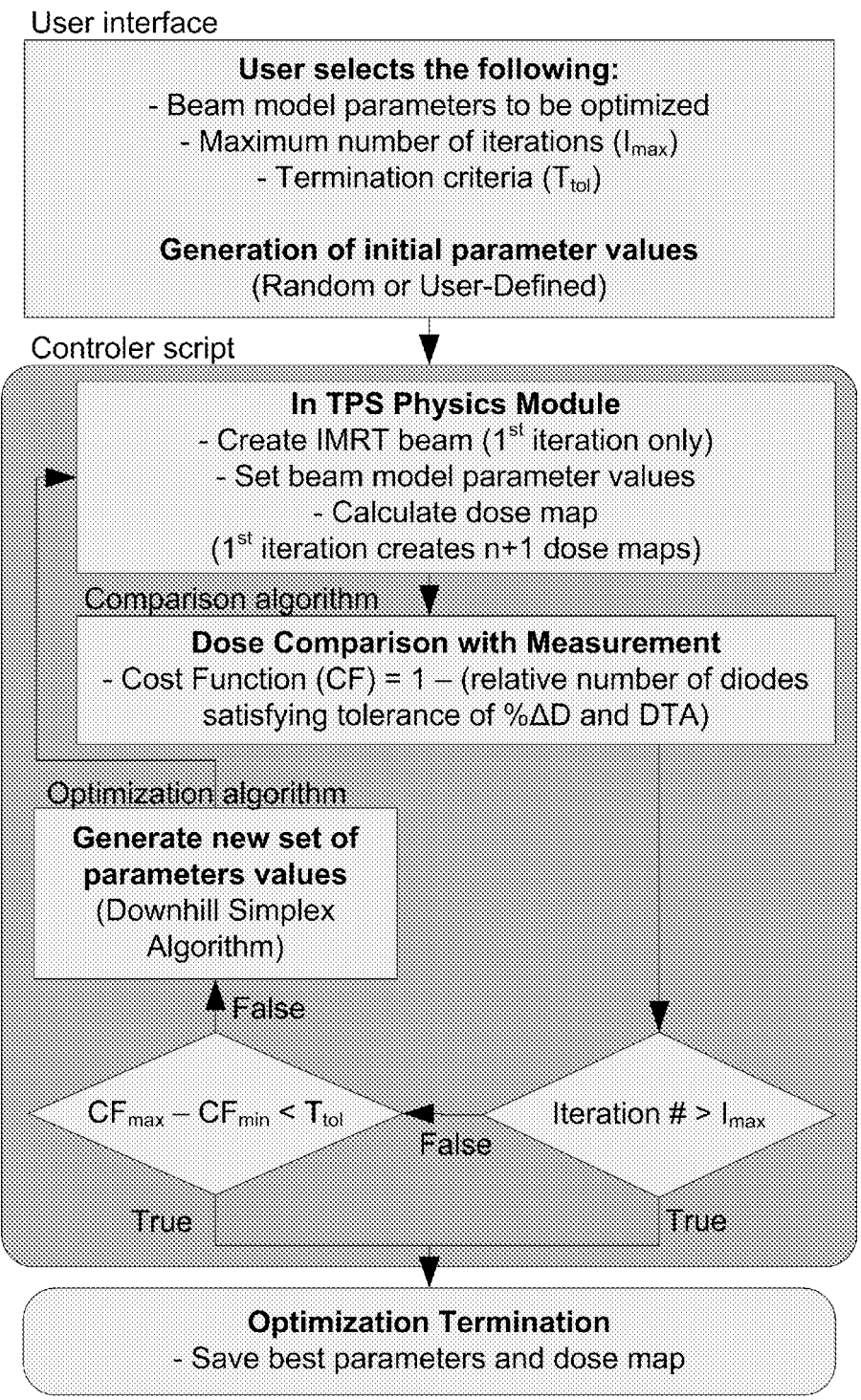
FIG. 1 is a flowchart showing an example method for commissioning a beam model for a 3D TPS, using an iterative technique.

In some aspects, a system and method for commissioning of a beam model for a three dimensional (3D) radiation therapy treatment planning system (TPS) is described. The disclosed system includes an intensity modulated radiotherapy (IMRT) unit (e.g., including a linear accelerator and a collimator) for generating a two dimensional (2D) intensity modulated beam pattern and a 2D diode array for detecting a 2D dose map for the beam pattern. The detected 2D dose map is used for iteratively calculating one or more parameters for the beam model. The system also includes a processor configured to execution instructions for iteratively adjusting one or more parameters for the beam model based on the dose map. In particular, the processor may iteratively adjust the beam model parameter(s) in order to increase, improve or maximize agreement between the dose map measured by the 2D diode array and the dose map calculated using the beam model. In particular, the processor may be configured to carry out the disclosed method for commissioning of a beam model.

The IMRT unit and the 2D diode array may be similar to those used for post-treatment planning patient-specific verification. The IMRT unit and the 2D diode array typically are not used for commissioning or optimization of a beam model. In some examples, a conventional TPS typically is not configured to accept such 2D data. Although the disclosed method and system is described as being for commissioning a beam model, the disclosed method and system may also be used to improve or optimize an existing beam model that was commissioned using conventional methods.

Conventionally, the commissioning of a TPS beam model consists of determining the beam model parameters that generate a reasonable fit between delivered and planned dose in simple irradiation conditions. The measurements used for commissioning typically include beam profiles and percent-depth dose (PDD) curves or tissue-phantom ratios obtained for square or rectangular open beams. These measurements are typically uni-dimensional in nature and sample only one axis of the radiation beam. During the beam model commissioning, the user manually adjusts the beam model parameters in an iterative approach to minimize differences between the calculated dose based on the beam model and the actual measured dose. The result of this commissioning depends on the user's ability to manage multiple parameters and assess their impact on the agreement between several measured and calculated dose profiles and PDDs. Two-dimensional dose maps obtained with a detector array have not conventionally been used for TPS beam model commissioning due to the relative novelty of this type of radiation detector and the limited ability of the TPS to import and use two-dimensional dose maps. The use of intensity modulated beam patterns for TPS beam model commissioning is not conventionally done. The development of two-dimensional detector arrays facilitated relatively accurate measurements of dose maps for intensity modulated beam patterns. Before replacing open beam irradiation for beam model commissioning with intensity modulated beam pattern, it may be useful to demonstrate the sensitivity of this type of beam delivery to variations of various beam model parameters. As well, TPS beam model modules may require reconfiguration to accept intensity modulated beam pattern for commissioning.

In the present disclosure, although the terms "optimized" or "optimization" are used, such terms may not necessarily indicate or require that the beam model is optimal or perfect. Rather, "optimized" or "optimization" should be understood to mean that the beam model has been commissioned or improved to meet a certain desired quality standard, although further improvements may still be possible.

Figure 3A:
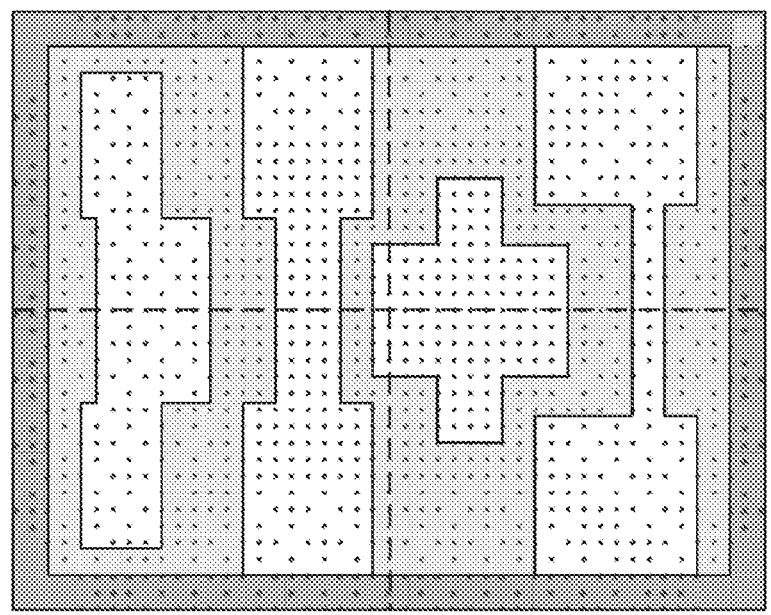
FIGS. 3A-3C illustrate an example beam pattern suitable for commissioning a beam model, and also illustrate example calculated dose maps for the beam pattern.
Figure 3B:
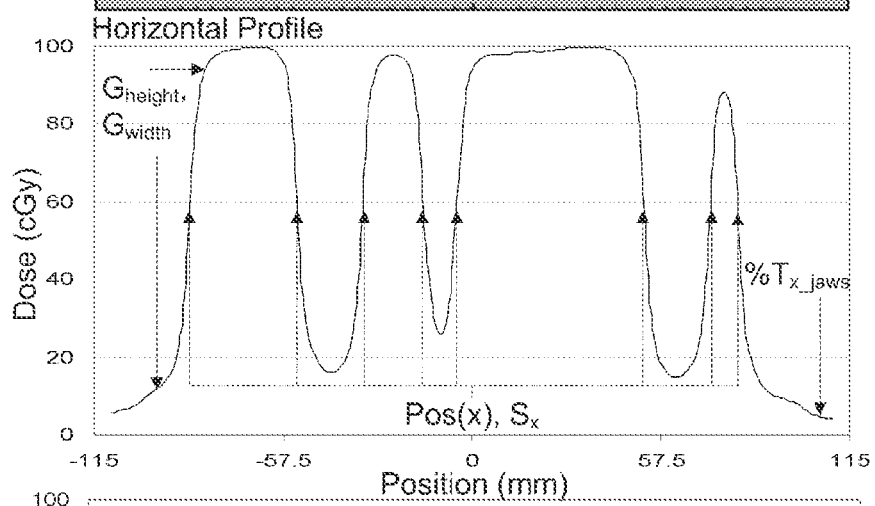
Figure 3C:
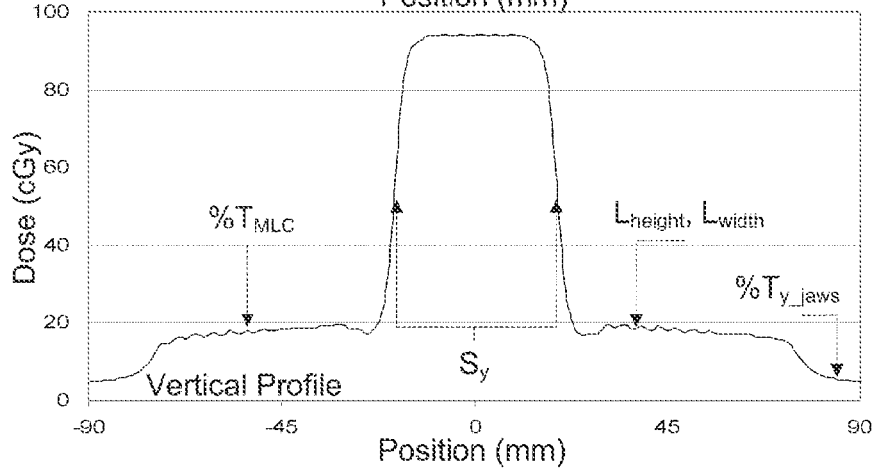

An example IMRT beam pattern suitable for beam model commissioning is shown in FIG. 3A. The example beam pattern may be generated by an example IMRT unit, including 4 step-and-shoot multi-leaf collimator (MLC) segments each delivering 100 monitor units (MU). FIGS. 3B and 3C illustrate example regions of the calculated dose map for the IMRT beam pattern sensitive to variation of specific beam model parameters, as indicated on horizontal and vertical calculated dose profiles, respectively. In this example, the beam pattern was designed to include irregular segment shapes and sizes in order to emphasis the variation of beam output and profile shape across the calculated dose map. The segment edges (i.e., penumbra) were distributed in horizontal and vertical directions across the maximum field aperture to ensure sensitivity to variation in source size, extra-focal radiation contribution and rounded leaf-end correction. The summation of multiple segments contributed to highlight radiation transmission through jaws and MLC (inter and intra-leaf) as well as the extra-focal radiation contribution[9,35]. The measured dose map for the IMRT beam pattern was acquired with an example 2D diode array (e.g., MapCheck, Sun Nuclear Corporation, Melbourne, Fla.), in this example using a source-to-array distance of 95 cm and a total of 5 cm of water-equivalent buildup material, which may correspond to the irradiation conditions used in conventional patient-specific IMRT verification. In this example, the density of measurement points may be increased by combining 5 diode array measurements, each performed with a 5 mm translation in right-to-left (RL) and superior-to-inferior (SI) directions. This may decrease the minimum linear distance between diodes from 14.1 and 7.1 mm in the native array geometry to 7.1 and 5 mm in the final measured dose map (e.g., as shown in the dot pattern in FIG. 3A).

Other IMRT beam patterns may be used, such as depending on the specific radiation therapy (e.g., different beam patterns may be suitable for different radiation therapy targets). In some examples, a combination of different beam patterns may be used. Although the above example describes a certain example beam pattern and a certain example 2D diode array, variations may be used. Any conventional 2D diode array may be suitable, and may use other types of detectors (e.g., ion chamber or photodiodes, among others), other detector patterns, other detector densities and/or other detector spatial resolutions. The 2D diode array may be selected depending on the application (e.g., based on the spatial resolution desired).

The operation of an example system for commissioning a beam model is now described. In some examples, the example system may be referred to as the automated beam model optimization system (ABMOS). In this example, the system was designed to adjust selected beam model parameters (e.g., for a TPS such as Pinnacle[3], version 8.0h, Philips Medical Systems, Madison, Wis.) iteratively to maximize the agreement between measured and calculated 2D dose maps obtained for an IMRT beam pattern. The IMRT beam pattern may be generated by an IMRT unit, such as the example described above, and the 2D dose maps acquired using a 2D diode array, such as the example described above. In this example, the system includes software modules for carrying out an example method for commissioning a beam model, which in this example was implemented in the UNIX operating system environment on the TPS workstation (dual AMD Opteron processor, 2.8 GHz). In this example, the software modules include the user-interface, the controller script, the dose comparison, and optimization algorithms. Other systems and/or software configurations may also be suitable.

An example method for commissioning and/or optimization of a beam model for a 3D TPS is now described, with reference to FIG. 1. In the example described, the method is carried out using software modules in the example system. In other examples, one or more of the method steps may be carried out separately from the system, for example using a separate workstation. The system may be configured to communicate data and calculations with other computing devices to carry out the example method. In some examples, the example method may be implemented in multi-core computers or graphic processing units, which may help speed up the computation and the commissioning of a beam model. The example method may be carried out using the disclosed system for commissioning a beam model, for example by the processor in the system.

FIG. 1 is a flowchart of an example method for commissioning a beam model for a 3D TPS, using an iterative technique. In this example, for each iteration, a processor (e.g., the processor of the disclosed system) created the IMRT beam used for the commissioning, set the beam model parameter values and calculated the corresponding dose map in a flat phantom. The calculated dose map is then compared in terms of dose difference (% ΔD) and distance to agreement (DTA) to a measured dose map obtained with a 2D diode array. The relative number of diodes which agreed with the calculated dose map within specified tolerances represents the pass rate. The cost function (CF) is equal to (1−pass rate). The iterative process is interrupted if the maximum number of iteration ($I_{max}$) is reached or if the maximum difference of CF for the nodes of the simplex is smaller than the termination criterion ($T_{tol}$).

At the initialization step of the example method, beam model parameters to be used in the commissioning, the maximum number of iterations ($I_{max}$) and the termination criterion ($T_{tol}$) are selected. In some examples, one or more of these selections may be made by the user, for example via a user-interface (e.g., written in Java). In other examples, one or more of these selections may be preset. These parameters are saved in an initialization file along with the filename containing the description (e.g., in TPS scripting language) of the IMRT beam pattern to be used in the optimization and the filename of the corresponding measured 2D dose map.

The initial beam model parameter values to be used in the commissioning are then randomly generated and added to the initialization file. These values may be limited to finite intervals (e.g., as specified by the TPS). The user may be provided with an option to manually edit these values before initiating the commissioning. The beam model parameters available for commissioning a beam model may include those compiled in the table of FIG. 2, for example, and may include those related to jaw and MLC transmission, radiation source size, extra-focal radiation contribution and/or MLC rounded leaf-end transmission, among others.

The commissioning or improvement of an existing or new beam model for a given virtual treatment unit may be performed within the TPS physics module by executing a controller script (e.g., using TPS scripting language). At the first iteration, the method generates the IMRT beam pattern to be used in the optimization. In this example, the downhill simplex algorithm[30], also referred to as the Nelder-Mead method, was used. This algorithm may be selected for its simplicity of implementation, and because it requires only function evaluations and no derivatives. Suitable algorithms that be used include: a downhill simplex algorithm, a gradient-based algorithm, and simulated-annealing, which may be used in combination with each other. Beam model commissioning typically is a constrained optimization problem as the beam model parameters are typically limited to finite intervals. In this example, it was re-formulated into an unconstrained problem using appropriate variable transformations[31]. For n beam model parameters, the downhill simplex algorithm requires n+1 sets of n initial values, which corresponds to the n+1 vertices of the simplex (n+1 by n matrix). During the first iteration, the n+1 sets of initial parameter values are alternately loaded in the beam model and the corresponding 2D dose maps are calculated in a homogenous flat phantom for the IMRT beam pattern and compared to the measured dose map. The relative number of measurement points which agreed with the calculated dose map within given tolerances of relative dose difference (% ΔD) and distance to agreement (DTA)[19, 32, 33] corresponds to the pass rate. The cost function is defined as (1−pass rate), which reformulates the optimization problem into a minimization process. The % ΔD tolerance was expressed as a function of the computed dose at a given measurement point and a maximum absolute ΔD of 1 cGy (e.g., based on the 2D array sensitivity) was used as an alternative pass criterion for low dose points[34]. The measurement points corresponding to <3% of the maximum dose on a dose map were excluded from the comparison to reduce favorable bias associated with low dose regions (inclusion threshold, % Th =3%). The optimization process stopped when $I_{max}$ was reached or when the maximum difference of cost function between the vertices of the simplex was inferior to $T_{tol}$.

The above describes an example method using an example algorithm for optimization of beam model parameters. However, other optimization algorithms may be used, and may include optimization of other beam model parameters (including parameters not listed in FIG. 2), according to different cost function and/or threshold measurements. For example a suitable category of optimization algorithms may include gradient-based algorithms or simulated annealing. Different optimization algorithms may offer different rates of convergence, and may be selected depending on the optimization problem. In some examples, optimization of beam model parameters may be based on more than one dose map acquired using more than one beam pattern. Variations may be made to the example method, such as to speed up the commissioning of the beam model.

For example, calculation of the 2D dose map may be a time-consuming calculation. This calculation may be sped up by implementing, for example, a non-uniform dose calculation grid with a higher calculation point resolution in the penumbra region and a lower calculation point resolution in the plateau region. In other examples, the method may only include dose map calculations for only a portion of the dose map and rely on symmetrical aspects of the beam pattern for the remaining portion.

Example Study

An example study is now described for evaluating and validating the performance of an example system, based on intensity modulated radiotherapy (IMRT) beam measurements, for the commissioning or the improvement of a beam model. The use of IMRT-type beams with multiple multi-leaf collimator (MLC) segments with large number of monitor units (MU) was selected to emphasize differences between planned and delivered dose and improve measured signal to noise ratio. The 2D diode array samples the entire beam with high-spatial resolution detectors in a single measurement. An example of the disclosed method and system was applied to the improvement of an existing beam model commissioned using conventional techniques. The impact of the beam model adjustments on the agreement between delivered and planned dose was studied extensively for 2 anatomic sites (paraspinal and prostate cancer) and 2 different methods of patient-specific IMRT QC.

In this example, a 2D diode array with high-spatial resolution detectors was used to sample the entire IMRT beam pattern in a single dose measurement. The use of an IMRT beam pattern with a large number of monitor units (MU) may highlight the difference between planned and delivered dose and improve the signal to noise ratio in the low dose regions. An example of the disclosed system and method was applied to the commissioning/improvement of a beam model for an Elekta Synergy S treatment unit. The resultant beam model was validated for two anatomic sites (25 paraspinal and 25 prostate cases) using two independent patient-specific IMRT quality control (QC) methods based on ion chamber and 2D diode array measurements, respectively. After beam model optimization with the example system, improvement in planned to delivered dose agreement was demonstrated with both patient-specific IMRT QC methods. The relative difference between ion chamber measurements and the planned dose (high and low dose points) was compiled for the 25 paraspinal SBRT and 25 prostate plans calculated with the initial and the optimized beam model. The largest improvement was observed for the paraspinal cases with the mean measured to calculated dose difference at the low dose points decreasing from −13.8% to 2.0% with the optimized beam model. The 2D diode array patient-specific quality control (QC) also demonstrated improvements in beam model for both paraspinal and prostate cases with on average more than 96% of the diodes satisfying tolerances of 3% of dose difference or 2 mm of distance to agreement after beam model improvement using an example of the disclosed method and system. Elements of statistical process control (SPC) were applied to the process of patient-specific QC performed with the ion chamber and the 2D array to complement the model comparison. Optimization of other beam models may also be possible.

The performance of an example of the disclosed system and method was assessed by optimizing the existing 6 MV photon beam model for a Synergy S treatment unit (Elekta Inc, Crawley, UK) with a fixed jaw design and a 4 mm leaf width MLC. This treatment unit has been used for the treatment of prostate cancer patients as well as for the delivery of a range of intra and extra-cranial stereotactic radiotherapy techniques. The existing clinically-approved beam model, referred to as the "initial beam model" in this disclosure, went through conventional manual beam modeling. The beam model optimization was performed with a combination of beam parameters (e.g., jaw and MLC transmission, source size and rounded leaf-end correction) and was repeated 11 times with different initial parameter values to better sample the cost function space and to avoid being caught in a local minimum. A pass rate of 85% or more was considered as an acceptable measured to calculated dose map agreement for tolerances of 2%/1 mm (% ΔD/DTA). The resulting beam model with the highest pass rate may be referred to as the "optimized beam model" in this disclosure, although "optimized" in this disclosure does not necessarily require that the beam model is optimal or perfect, only that the beam model may satisfy certain quality standards.

The optimized beam model for the example Synergy S unit was evaluated by retrospectively re-computing the dose for clinical plans with the new model and comparing the results to the original patient-specific QC measurements. Standard patient-specific QC in this example includes two dose point measurements in high and low dose regions (target and organ at risk) using a Farmer-type ion chamber inserted in a 20 cm diameter cylindrical solid water phantom[36]. Differences between measured and calculated dose points were compared for the initial and optimized beam models for 25 paraspinal stereotactic body radiotherapy (SBRT) and 25 prostate plans. These sites are both treated, in this example, with a 6 MV IMRT technique using 7 and 9 coplanar beams, respectively, and are representative of the clinical use of the Synergy S unit. Individual beam measurements were retrospectively performed with a 2D diode array (MapCheck, Sun Nuclear Corporation, Melbourne, Fla.) as a second independent patient-specific QC for the 25 paraspinal SBRT and 25 prostate cases included in this example study. For each beam, the relative number of diodes which agreed with the calculated dose map within 3%/2 mm or 2%/1 mm and an inclusion threshold % Th=10% was obtained for both initial and optimized beam models. The mean pass rate and standard deviation (SD) were compiled for the two beam models.

Elements of statistical process control (SPC) were applied to the process of patient-specific QC performed with the Farmer chamber and the 2D array to complement the model comparison. The variations observed in this process in terms of measured to calculated dose difference at a point or in terms of diode pass rate depends on the beam model, the experimental dose measurements and the treatment unit mechanical and dosimetric calibration. For the 2D diode array measurements, the non-conforming fraction[37] represents the relative number of diodes that did not satisfy given tolerances of % ΔD and DTA (1−pass rate). Proportional control charts (p-chart)[37] are used to illustrate the variation in non-conforming fraction as a function of beam number for the 25 paraspinal SBRT and 25 prostate plans calculated with both the initial and optimized beam models. The upper and lower control limits (UCL and LCL) on a p-chart represent the maximum allowable variation in the relative number of diodes, which did not satisfy given tolerance of % ΔD and DTA and can be calculated using Eq. 1. The mean non-conforming fraction (p) and the range of UCL and LCL were used to compare the initial and the optimized beam models. The Farmer chamber and 2D array measurements were also used to calculate the capability index ($C_{pk}$) of the patient-specific QC for the planning and delivery of paraspinal SBRT and prostate plans. $C_{pk}$, which is defined as the ratio of the observed and tolerable variability of a process, was calculated using Eq. 2 and 3 [37] for normal and non-normal distributions, respectively.

Figure 4A:
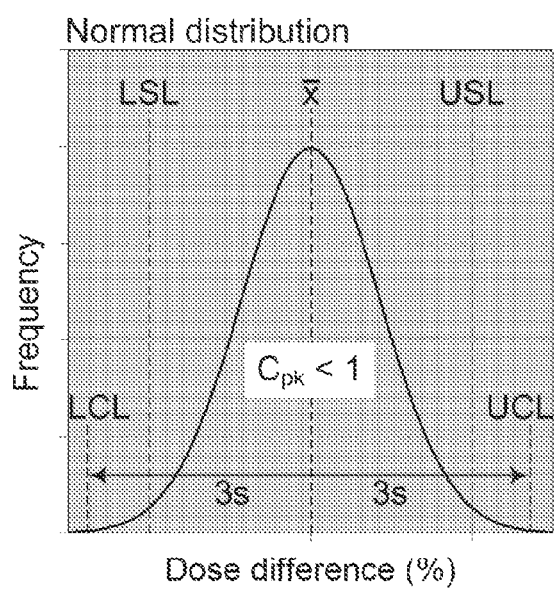
FIG. 4A and 4B illustrate the calculation of a capability index ($C_{pk}$) which may be suitable for use as a quality measurement, in some examples.
Figure 4B:
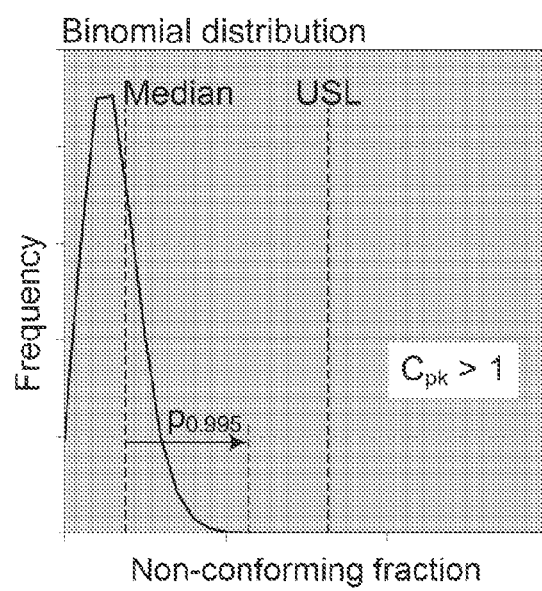

The concept of $C_{pk}$ is illustrated in FIG. 4A and FIG. 4B for hypothetical processes following a normal and a binomial distribution, respectively. In FIG. 4A, the normally distributed process (hypothetical measured to calculated dose difference at a point) is deemed incapable ($C_{pk}$<1) as the range of lower and upper specification limits (LSL and USL) is smaller than the range of lower and upper control limits (LCL and UCL). LCL and UCL correspond to 3 standard deviations (3s) around the mean ($\bar{x}$) of the distribution. In FIG. 4B, the hypothetical non-conforming fraction for the patient-specific QC performed with the 2D array is deemed capable ($C_{pk}$>1) as the range between the median of the distribution and the USL is larger than the range between the median and the 99.5$^{th}$ percentile ($p_{0.995}$) of the distribution.

For a given beam model, an increase in $C_{pk}$ corresponds to an improvement in measured to calculated dose agreement.

$$UCL = p + 3\sqrt{\frac{p(1-p)}{n}} \text{ and } LCL = p - 3\sqrt{\frac{p(1-p)}{n}} \quad \text{Eq. 1}$$

Where $p$ = mean non-conforming fraction
i. $n$ = total number of diodes sampling a beam $$C_{pk} = \min\left[\frac{USL - \bar{x}}{3s}, \frac{\bar{x} - LSL}{3s}\right] \quad \text{Eq. 2}$$

$$C_{pk} = \min\left[\frac{USL - \text{median}}{p_{0.995} - \text{median}}, \frac{\text{median} - LSL}{\text{median} - p_{0.005}}\right] \quad \text{Eq. 3}$$

Where $\bar{x}$ is the mean for the distribution of measured to calculated dose difference obtained with the Farmer chamber measurements and for the distribution of non-conforming fraction for the 2D array diode measurements.

ii. LSL and USL are the lower and upper specification limits or tolerances.

iii. s is the standard deviation for the distribution of measured to calculated dose difference obtained with the Farmer chamber measurements and for the distribution of non-conforming fraction obtained with the 2D array diode measurements.

$p_{0.995}$ and $p_{0.005}$ are the 99.5 and 0.5 percentile for the distribution of measured to calculated dose difference obtained with the Farmer chamber and for the distribution of non-conforming fraction obtained with the 2D diode array.

FIG. 3A illustrates an example IMRT beam pattern used for commissioning of the beam model. The example beam pattern contained 4 segments delivering 100 monitor units (MU) each. The light and dark gray area represents the portion of the field shielded by the MLC and the jaws and MLC, respectively. The dots represent the example diode pattern used for the measurement of this example IMRT beam. Horizontal and vertical profiles extracted from the corresponding calculated dose map (along dash lines in FIG. 3A) are shown in FIG. 3B and FIG. 3C, respectively. Regions of the calculated IMRT dose map sensitive to specific beam model parameters are identified on the horizontal and vertical profiles using the beam model parameter abbreviations described in FIG. 2.

The example Synergy S beam model was optimized using the example system and 5 out of the 6 beam model parameters shown in FIG. 2 (jaw and MLC transmission, MLC interleaf leakage, source size and rounded leaf-end correction). The example beam model parameter values for the initial and the optimized beam model are compared in the table of FIG. 5. After optimization, the pass rate for the example IMRT beam pattern shown in FIG. 3A increased from 46.1% (conventionally commissioned beam model) to 87.3% (using example of disclosed method and system) for tolerances of 2%/1 mm and % Th=3%. Variation in pass rate of 63.3% to 87.3% for 11 optimizations performed with different initial parameter values (excluding the extra-focal radiation contribution parameter) empirically demonstrated the presence of local minima in the cost function. Three out of the 11 optimizations generated a pass rate superior to 85%. The time duration for carrying out the example method varied from about 9 to 16 hours for 156 to 256 iterations.

The relative difference between Farmer chamber measurements and the planned dose at the same point was compiled in the table of FIG. 6 for the 25 paraspinal SBRT and 25 prostate plans calculated with the conventional and the optimized beam model. In FIG. 6, the measured dose was obtained with a Farmer-type ionization chamber. The optimized model was found to improve the measured to calculated dose agreement in the low dose region for both treatment sites. For the high dose point located in the target, the mean measured to calculated dose difference decreased from −4.2% to −0.3% for the paraspinal SBRT cases using the optimized beam model while it increased by 0.5% for the prostate plans. The hypofractionated paraspinal SBRT plans (6 to 18 Gy/fraction) were more sensitive to the variation of MLC transmission and interleaf leakage parameters than the prostate cases due to the high number of MU delivered per beam. The patient-specific QC performed with the 2D diode array also clearly demonstrated the improvement in beam model after optimization using ABMOS. For example, the table of FIG. 7 shows a comparison of measured and calculated dose maps per beam for paraspinal and prostate plans. The relative number of diodes (pass rate), which agreed with the dose calculation for given tolerances of dose difference (% ΔD) and distance to agreement (DTA) was calculated for the initial and the optimized models. The inclusion threshold (% Th) was set to 10% for these comparisons. In FIG. 7, the measured dose was obtained with a two-dimensional diode array.

The mean diode pass rate (tolerance of 3%/2 mm and % Th=10%) increased from 77.1% to 96.4% with the optimized beam model for the 25 paraspinal SBRT plans and a total of 214 beams. Eleven paraspinal beams using 18 MV photons were excluded from the comparison. For the prostate cases (total of 175 beams), the mean diode pass rate reached 98.2% with the optimized beam model. For both sites, the incremental improvement in pass rate increased with tighter tolerances of 2%/1 mm (FIG. 7). The mean dose differences (FIG. 6) and the mean diode pass rates (FIG. 7) for the initial and optimized beam model were statistically different based on t-test and Wilcoxon signed rank test for normal and non-normal distribution (normality test: Shapiro-Wilk).

The variation in diode pass rate also decreased with the optimized beam model with a reduction in SD of 9.7% to 2.8% and 4.1% to 1.6% for the paraspinal SBRT and the prostate cases, respectively. For the measured to calculated point dose comparison, the reduction in SD with the optimized model was not as pronounced (FIG. 6) and this limited improvement was attributed to the finite volume of the Farmer chamber (0.6 cm$^3$) and the presence of dose gradients at the location of the dose measurements. For both models, the largest discrepancies between measured and calculated point dose (low dose region) were observed for thoracic/cervical spine cases for which the dose distribution is shaped to follow the curvature of the spine.

Reduction in mean and spread of the non-conforming fraction is shown on the p-charts of FIGS. 8A-8D and demonstrates improvement in process control (non-conforming fraction within upper and lower control limits) for the patient-specific QC using this example of the disclosed method and system (tolerance: 3%/2 mm). In FIGS. 8A-8D, the non-conforming fraction of diodes is shown as function of the beam number for the 25 prostate (FIGS. 8A and 8B) and paraspinal (FIGS. 8C and 8D) cases. The measured and calculated dose maps were compared for both the initial and the optimized beam models using the following tolerances: 3% of dose difference (% ΔD) or 2 mm of distance to agreement (DTA) and an inclusion threshold (% Th) of 10%.

Figure 9A:
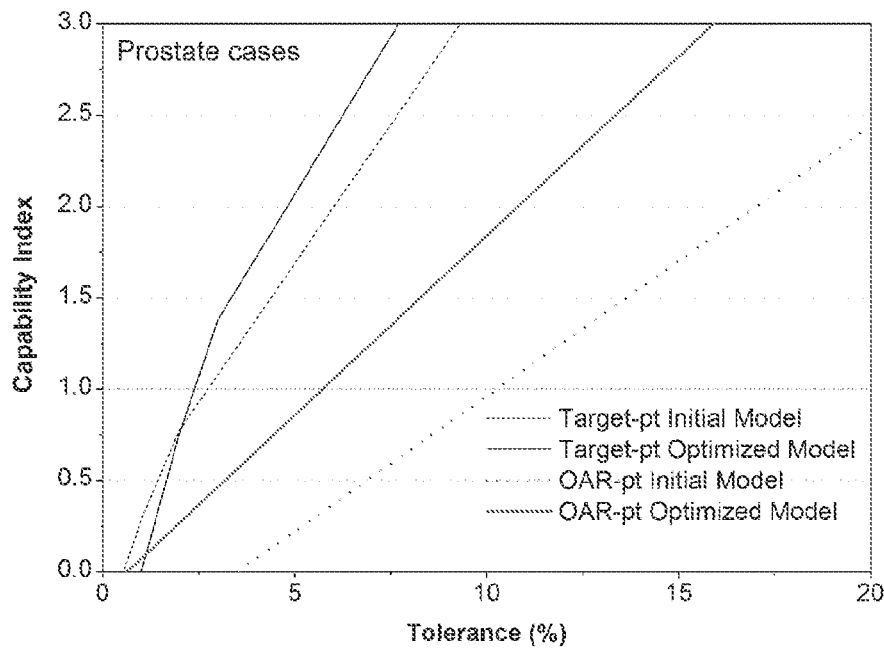
FIGS. 9A and 9B show charts comparing $C_{pk}$ of beam models commissioned using conventional methods and using an example of the disclosed method for commissioning a beam model for a 3D TPS.
Figure 9B:
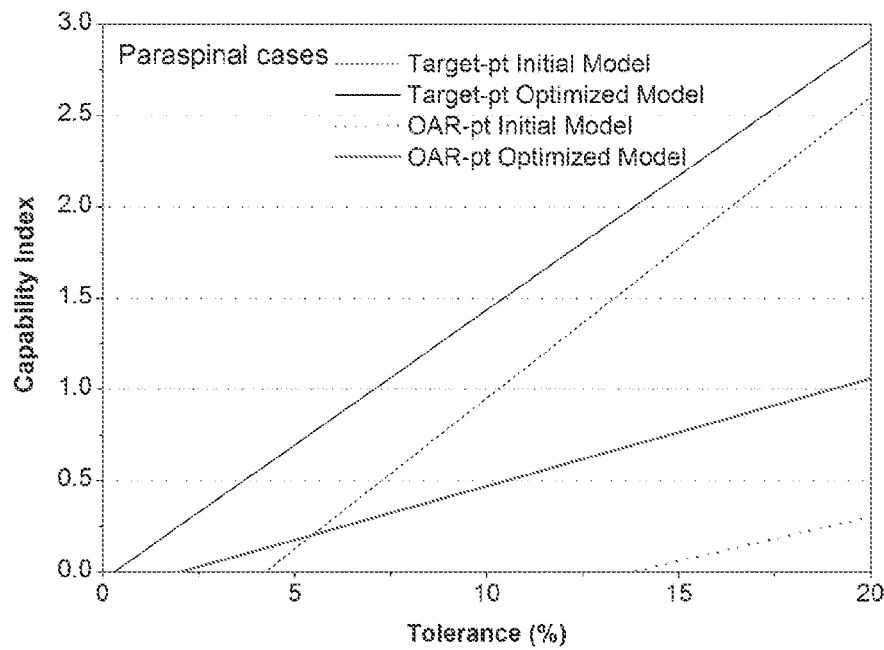
Figure 10:
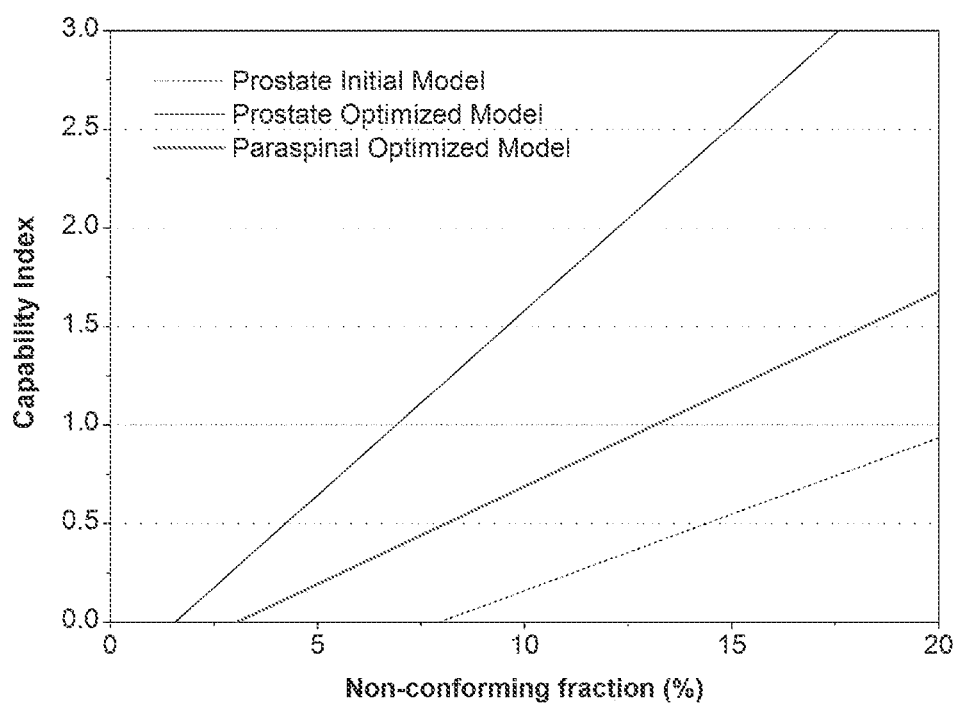
FIG. 10 shows charts comparing $C_{pk}$ of beam models commissioned using conventional methods and using an example of the disclosed method for commissioning a beam model for a 3D TPS.

The fraction of beams with a non-conforming fraction lower than the upper control limit increased from 90.7% to 97.2% and 92% to 94.3% with the optimized beam model for the 214 paraspinal and 175 prostate beams, respectively. In addition to the p-charts, $C_{pk}$ was used to compare the initial and optimized beam models as it relates the observed variations in the patient-specific QC process to tolerances specified by the user. FIGS. 9A and 9B and FIG. 10 show $C_{pk}$ as a function of user-defined dose difference tolerance for the ion chamber and the 2D diode array patient-specific QC, respectively. For FIGS. 9A and 9B, the capability index ($C_{pk}$) of the ion chamber-based patient specific QC was calculated as a function of the dose difference tolerated between the measured and the calculated dose in the target and the in an organ at risk. $C_{pk}$ was obtained for the prostate and the paraspinal cases for both the initial and optimized beam model. For FIG. 10, the capability index ($C_{pk}$) of the 2D diode array-based patient specific QC was calculated as a function of the tolerated non-conforming fraction. $C_{pk}$ was obtained for the prostate and the paraspinal cases (175 and 217 beams, respectively) for both the initial and optimized beam model. The tolerance used for the measured to calculated dose map comparison were 3% of dose difference (% ΔD) or 2 mm of distance to agreement (DTA) and an inclusion threshold (% Th) of 10%.

For a capable QC process ($C_{pk}$=1), the required dose difference tolerance (high dose point) with the optimized beam model decreased from about 10.5% to 7.0% for the paraspinal cases while it remained around 2-3% for the prostate plans (FIGS. 9A and 9B). Substantial reduction in dose difference tolerance was also observed for the low dose point measurements for both sites but it remained high (almost 19%) for the paraspinal plans due to the large dose differences observed for the thoracic/cervical cases with rotated dose distribution (FIGS. 9A and 9B). For the 2D diode array measurement and the optimized beam model, the tolerance on the non-conforming fraction required to deem the QC process capable ($C_{pk}$=1) also decreased substantially and dropped from about 50% to 13.5% and 21% to 7.0% for the paraspinal and prostate beams, respectively (FIG. 10, tolerance 3%/2 mm).

The example study demonstrates improvement in beam model accuracy using an example system and method. The disclosed system and method differs from the existing auto-scripts in a conventional TPS as the disclosed system and method use 2D dose maps of an IMRT beam pattern for commissioning a beam model instead of individual profiles of static beams, as in conventional techniques. Multi-variable optimizations of the beam model were performed, since the calculated dose map for the IMRT beam pattern used in this example study demonstrated sensitivity to variations of various beam model parameters. The diode pass rate (for a given tolerance of % ΔD and DTA) represented a simple numeric metric of the measured to calculated dose map agreement and was readily usable in the example optimization algorithm cost function. In addition, the large total number of MU associated with the multi-segment beam increased the measured signal in low dose region and allowed modeling of jaw and MLC transmission parameters with higher reliability. The example system and method also allowed for single parameter optimizations, which may be useful to study the impact of individual beam model parameter on dose calculation. As pointed out by Starkschall et al[18], understanding of the TPS dose calculation algorithm and its beam model parameters is useful for its commissioning. For example, understanding the physical meaning of the beam model parameters in Pinnacle[3] may help the user choose meaningful initial values for the optimization algorithm, and may help identify optimization results, which correspond to sub-optimum local minima in the cost function.

The example implementation of a paraspinal SBRT technique and the application of patient-specific IMRT QC for these cases uncovered some limitations in the conventional beam model of the example Synergy S treatment unit that were not as apparent for prostate plans. These results demonstrated that demands on a beam model can be different for various clinical IMRT applications[36]. Visual comparison of paraspinal and prostate plans typically showed that paraspinal IMRT beams consisted of multiple small abutting MLC segments instead of an open MLC segment with few superimposed small segments for prostate beams. The MLC segment patterns of abutting fields and the large number of MU for the hypofractionated paraspinal plans increased the dosimetric importance of the inter and intra-leaf MLC transmissions on the dose distribution. Paraspinal plans were also more sensitive to fine adjustments of the beam model source size and the TPS rounded leaf-end correction as the penumbrae of the abutting MLC segments were added together to create the IMRT beam fluence. These results demonstrated the usefulness of commissioning and/or validating new beam models for more than one anatomic site. Furthermore, the use of two independent dosimeters for the assessment of a newly optimized beam model may help overcome individual detector limitations. For example, ion chamber dose measurements may have the advantage to directly assess the composite dose distribution at a given point. However, the Farmer chamber volume (0.6 cm³) may make accurate point dose measurements challenging for some paraspinal dose distributions that were highly irregular in shape (upper thoracic and cervical cases). The disclosed method and system, using an example 2D diode array, solved the spatial resolution problem related to the chamber and the beam sampling at multiple points demonstrated an improvement in beam model over conventional methods. The ion chamber based patient-specific QC still remained a step in the validation of the optimized model as it is independent from commissioning of the beam model.

The optimized beam model obtained with the example system for the example Synergy S treatment unit was found to improve the capability ($C_{pk}$) of both ion chamber and 2D array patient-specific QC methods for the paraspinal and prostate plans. Tolerances on patient-specific QC results for a given IMRT application should be representative of acceptable clinical dose limits, available geometric margins, and treatment unit and dosimeter performances. Tolerances for the ion chamber and 2D array patient-specific QC processes can also be estimated for a given value of $C_{pk}$ (for example, $C_{pk}$=1) using SPC theory. These tolerances are calculated based on a realistic estimate of the variability in patient-specific QC results (dose difference or pass rate). For a given patient-specific QC method, the SPC and clinical tolerances can be compared to assess if the QC process is likely to satisfy the clinical specifications. For the ion chamber measurements, the QC process capability may be limited by the chamber's volume and the irregular shape of the paraspinal dose distributions, especially for the measurements in low dose region. Improvement in patient-specific QC process capability for the 2D diode array could potentially be achieved with tighter MLC calibration tolerance (e.g. 0.5 mm) and improvement in diode array calibration. Setting up the detector array using CBCT image guidance instead of aligning it on room lasers could also reduced positioning uncertainty during QC measurements and have a positive impact on QC results[34, 40, 41].

The optimized beam model obtained from the example study has also been used for treatment planning for 20 paraspinal patients. The measured to calculated dose difference for the ion chamber QC (both high and low dose points) was within ±5% for 18 out of these 20 cases. This good measured to calculated dose agreement contributed to reduce the user workload related to dose difference investigation and repeat QC measurements. In some examples, the system has been modified to perform beam model commissioning on other photon energies (10 and 18 MV) and other treatment unit brands. Variation in linear accelerator head designs (e.g. dynamic versus static jaws) and IMRT application between treatment units might require the design of one or more different IMRT beam patterns.

A system and method for commissioning a beam model for a three dimensional radiation therapy treatment planning system was described. An example study was also described, using an example of the disclosed system and method, specifically an example system based on IMRT beam pattern measurements performed with a two dimensional (2D) diode array for the commissioning or the improvement of a beam model. The use of an IMRT beam pattern in the optimization highlighted differences between planned and delivered dose and the 2D diode array offered relatively high-spatial resolution detectors and samples the entire beam in a single measurement. In the example study, an example system and method was applied to the beam model optimization of an Elekta Synergy S treatment unit. The improvement in the beam model after optimization using the example system and method was demonstrated for two anatomic sites (paraspinal and prostate cancer) using two independent methods of patient-specific IMRT QC. Based on the observed improvements in patient-specific QC results for 25 paraspinal and 25 prostate plans, improvement of other beam models using the disclosed method and system is expected.

Although the above examples describe the use of the Pinnacle[3] TPS, the disclosed method and system may also be suitable for use with other TPS. The dose calculation algorithm may also be varied, for example depending on the TPS, and may include algorithms such as a pencil beam algorithm or a Monte Carlo algorithm.

Although the present disclosure includes description of certain examples, details and ranges, these are for the purpose of illustration only and are not intended to be limiting. Features described in separate examples and embodiments may be combined. For any ranges described, specific values or ranges within the disclosed ranges are also disclosed. Variations may be possible within the scope of the present disclosure. Any theory, model or calculations described are for the purpose of illustration only and the present disclosure is not bound to these. All references mentioned are hereby incorporated by reference in their entirety.

References

1. T. Bortfeld, W. Schlegel, B. Rhein, "Decomposition of pencil beam kernels for fast dose calculations in three-dimensional treatment planning," Med Phys. 20, 311-318 (1993).

2. J. D. Bourland, E. L. Chaney, "A finite-size pencil beam model for photon dose calculations in three dimensions," Med Phys. 19, 1401-1412 (1992).

3. A. Gustafsson, B. K. Lind, A. Brahme, "A generalized pencil beam algorithm for optimization of radiation therapy," Med Phys. 21, 343-356 (1994).

4. O. Z. Ostapiak, Y. Zhu, J. Van Dyk, "Refinements of the finite-size pencil beam model of three-dimensional photon dose calculation," Med Phys. 24, 743-750 (1997).

5. A. Ahnesjo, "Collapsed cone convolution of radiant energy for photon dose calculation in heterogeneous media," Med Phys. 16, 577-592 (1989).

6. T. R. Mackie, J. W. Scrimger, J. J. Battista, "A convolution method of calculating dose for 15-MV x rays," Med Phys. 12, 188-196 (1985).

7. N. Papanikolaou, T. R. Mackie, C. Meger-Wells, M. Gehring, P. Reckwerdt, "Investigation of the convolution method for polyenergetic spectra," Med Phys. 20, 1327-1336 (1993).

8. J. J. Battista, M. B. Sharpe, "True three-dimensional dose computations for megavoltage x-ray therapy: a role for the superposition principle," Australas Phys Eng Sci Med. 15, 159-178 (1992).

9. M. B. Sharpe, D. A. Jaffray, J. J. Battista, P. Munro, "Extrafocal radiation: a unified approach to the prediction of beam penumbra and output factors for megavoltage x-ray beams," Med Phys. 22, 2065-2074 (1995).

10. J. J. DeMarco, T. D. Solberg, J. B. Smathers, "A CT-based Monte Carlo simulation tool for dosimetry planning and analysis," Med Phys. 25, 1-11 (1998).

11. D. M. Lovelock, C. S. Chui, R. Mohan, "A Monte Carlo model of photon beams used in radiation therapy," Med Phys. 22, 1387-1394 (1995).

12. C. M. Ma, E. Mok, A. Kapur, T. Pawlicki, D. Findley, S. Brain, K. Forster, A. L. Boyer, "Clinical implementation of a Monte Carlo treatment planning system," Med Phys. 26, 2133-2143 (1999).

13. D. W. Rogers, B. A. Faddegon, G. X. Ding, C. M. Ma, J. We, T. R. Mackie, "BEAM: a Monte Carlo code to simulate radiotherapy treatment units," Med Phys. 22, 503-524 (1995).

14. L. Wang, C. S. Chui, M. Lovelock, "A patient-specific Monte Carlo dose-calculation method for photon beams," Med Phys. 25, 867-878 (1998).

15. A. Ahnesjo, L. Weber, A. Murman, M. Saxner, I. Thorslund, E. Traneus, "Beam modeling and verification of a photon beam multisource model," Med Phys. 32, 1722-1737 (2005).

16. F. M. Khan. The Physics of Radiation Therapy. Second ed. Baltimore, Md., USA: Williams and Wilkins; 1994.

17. B. Fraass, K. Doppke, M. Hunt, G. Kutcher, G. Starkschall, R. Stern, J. Van Dyke, "American Association of Physicists in Medicine Radiation Therapy Committee Task Group 53: quality assurance for clinical radiotherapy treatment planning," Med Phys. 25, 1773-1829 (1998).

18. G. Starkschall, R. E. Steadham, Jr., R. A. Popple, S. Ahmad, Rosen, II, "Beam-commissioning methodology for a three-dimensional convolution/superposition photon dose algorithm," J Appl Clin Med Phys. 1, 8-27 (2000).

19. J. Van Dyk, R. B. Barnett, J. E. Cygler, P. C. Shragge, "Commissioning and quality assurance of treatment planning computers," Int J Radiat Oncol Biol Phys. 26, 261-273 (1993).

20. J. Venselaar, H. Welleweerd, B. Mijnheer, "Tolerances for the accuracy of photon beam dose calculations of treatment planning systems," Radiother Oncol. 60, 191-201 (2001).

21. J. L. Bedford, P. J. Childs, V. Nordmark Hansen, M. A. Mosleh-Shirazi, F. Verhaegen, A. P. Warrington, "Commissioning and quality assurance of the Pinnacle (3) radiotherapy treatment planning system for external beam photons," Br J Radiol. 76, 163-176 (2003).

22. A. Rangel, N. Ploquin, I. Kay, P. Dunscombe, "Towards an objective evaluation of tolerances for beam modeling in a treatment planning system," Phys Med Biol. 52, 6011-6025 (2007).

23. W. A. Tome, "Beam modeling for a convolution/superposition-based treatment planning system," Med Dosim. 27, 11-19 (2002).

24. W. U. Laub, T. Wong, "The volume effect of detectors in the dosimetry of small fields used in IMRT," Med Phys. 30, 341-347 (2003).

25. G. Yan, C. Fox, C. Liu, J. G. Li, "The extraction of true profiles for TPS commissioning and its impact on IMRT patient-specific QA," Med Phys. 35, 3661-3670 (2008).

26. E. L. Chang, A. S. Shiu, E. Mendel, L. A. Mathews, A. Mahajan, P. K. Allen, J. S. Weinberg, B. W. Brown, X. S. Wang, S. Y. Woo, C. Cleeland, M. H. Maor, L. D Rhines, "Phase I/II study of stereotactic body radiotherapy for spinal metastasis and its pattern of failure," J Neurosurg Spine. 7, 151-160 (2007).

27. P. C. Gerszten, S. A. Burton, C. Ozhasoglu, W. C. Welch, "Radiosurgery for spinal metastases: clinical experience in 500 cases from a single institution," Spine (Phila Pa. 1976). 32, 193-199 (2007).

28. A. Sahgal, C. Ames, D. Chou, L. Ma, K. Huang, W. Xu, C. Chin, V. Weinberg, C. Chuang, P. Weinstein, D. A. Larson, "Stereotactic body radiotherapy is effective salvage therapy for patients with prior radiation of spinal metastases," Int J Radiat Oncol Biol Phys. 74, 723-731 (2009).

29. Y. Yamada, M. H. Bilsky, D. M. Lovelock, E. S. Venkatraman, S. Toner, J. Johnson, J. Zatcky, M. J. Zelefsky, Z. Fuks, "High-dose, single-fraction image-guided intensity-modulated radiotherapy for metastatic spinal lesions," Int J Radiat Oncol Biol Phys. 71, 484-490 (2008).

30. J. A. Nelder, R. Mead, "A simplex method for function minimization," Computer Journal. 7, 308-313 (1965).

31. A. Antoniou, W. S. Lu. Practical Optimization. Algorithms and Engineering Applications. New York: Springer; 2007.

32. ICRU. Use of computers in external beam radiotherapy procedures with high-energy photons and electrons. Report No 42. Washington, D.C.: International Commission on Radiation Units and Measurements; 1987.

33. A. S. Shiu, S. Tung, K. R. Hogstrom, J. W. Wong, R. L. Gerber, W. B. Harms, J. A. Purdy, R. K. Ten Haken, D. L. McShan, B. A. Fraass, "Verification data for electron beam dose algorithms," Med Phys. 19, 623-636 (1992).

34. D. Letourneau, H. Keller, M. B. Sharpe, D. A. Jaffray, "Integral test phantom for dosimetric quality assurance of image guided and intensity modulated stereotactic radiotherapy," Med Phys. 34, 1842-1849 (2007).

35. D. A. Jaffray, J. J. Battista, A. Fenster, P. Munro, "X-ray sources of medical linear accelerators: focal and extra-focal radiation," Med Phys. 20, 1417-1427 (1993).

36. S. L. Breen, D. J. Moseley, B. Zhang, M. B. Sharpe, "Statistical process control for IMRT dosimetric verification," Med Phys. 35, 4417-4425 (2008).

37. D. E. Lighter, D. C. Fair. Principles and Methods of Quality Management in Health Care. Gaithersburg, Md.: Aspen; 2000.

38. D. Letourneau, M. Gulam, D. Yan, M. Oldham, J. W. Wong, "Evaluation of a 2D diode array for IMRT quality assurance," Radiother Oncol. 70, 199-206 (2004).

39. MapCHECK User's Guide. Melbourne, Fla., USA: Sun Nuclear Corporation; 2004.

40. D. Letourneau, J. Publicover, J. Kozelka, D. J. Moseley, D. A. Jaffray, "Novel dosimetric phantom for quality assurance of volumetric modulated arc therapy," Med Phys. 36, 1813-1821 (2009).

41. C. G. Rowbottom, D. A. Jaffray, "Development of an integral system test for image-guided radiotherapy," Med Phys. 31, 3500-3505 (2004).

The invention claimed is:

1. A system for commissioning of a beam model comprising a virtual mechanical and dosimetric representation of a treatment unit for use with a three dimensional radiation therapy treatment planning system, the system comprising:
 an intensity modulated radiotherapy (IMRT) unit for generating a two dimensional intensity modulated beam pattern;
 a two dimensional diode array for detecting a two dimensional dose map for the beam pattern; and
 a processor configured to execute instructions for iteratively adjusting one or more parameters of the beam model, in order to increase agreement between the detected dose map and a calculated dose map calculated using the beam model.

2. The system of claim 1 wherein the processor is further configured to iteratively adjust the one or more parameters of the beam model using an optimization algorithm.

3. The system of claim 2 wherein the optimization algorithm is one of: a downhill simplex algorithm, a gradient-based algorithm, simulated annealing and combinations thereof.

4. The system of claim 1 wherein the one or more parameters of the beam model include one or more of: multi-leaf collimator (MLC) transmission, jaw transmission, MLC interleaf leakage, orthogonal source size, extra-focal scatter source, and geometric correction for rounded leaf MLC leaf end.

5. The system of claim 1 wherein the beam pattern comprises a plurality of multi-leaf collimator (MLC) segments.

6. The system of claim 5 wherein the beam pattern comprises a maximum field aperture, and the plurality of multi-leaf collimator segments are distributed in horizontal and vertical directions across the maximum field aperture.

7. A method for commissioning of a beam model comprising a virtual mechanical and dosimetric representation of a treatment unit for use with a three dimensional radiation therapy treatment planning system, the method comprising:
 obtaining a measured two dimensional dose map for a two dimensional intensity modulated beam pattern;
 iteratively adjusting one or more parameters of the beam model, in order to increase agreement between the measured dose map and a calculated dose map calculated using the beam model.

8. The method of claim 7 further comprising:
 generating a two dimensional intensity modulated beam pattern using an intensity modulated radiotherapy (IMRT) unit; and
 acquiring the two dimensional dose map for the beam pattern using a two dimensional diode array for detecting a two dimensional dose map.

9. The method of claim 7 wherein the one or more parameters of the beam model are iteratively adjusted using an optimization algorithm.

10. The method of claim 9 wherein the optimization algorithm is one of: a downhill simplex algorithm, a gradient-based algorithm, simulated annealing and combinations thereof.

11. The method of claim 7 wherein the one or more parameters of the beam model include one or more of: multi-leaf collimator (MLC) transmission, jaw transmission, MLC interleaf leakage, orthogonal source size, extra-focal scatter source, and geometric correction for rounded leaf MLC leaf end.

12. The method of claim 7 wherein a plurality of dose maps is used for iteratively adjusting the one or more parameters of the beam model.

13. The method of claim 7 wherein the beam pattern comprises a plurality of multi-leaf collimator (MLC) segments.

14. The method of claim 13 wherein the beam pattern comprises a maximum field aperture, and the plurality of multi-leaf collimator segments are distributed in horizontal and vertical directions across the maximum field aperture.

* * * * *